United States Patent

Hirose et al.

[11] Patent Number: 5,807,908
[45] Date of Patent: Sep. 15, 1998

[54] IONIZING RADIATION-RESISTANT POLYCARBONATE RESIN COMPOSITION AND MEDICAL PART COMPRISING SAME

[75] Inventors: Yoshikazu Hirose; Naoyoshi Kawamoto; Shigeharu Suzuki, all of Osaka, Japan

[73] Assignee: Sumitomo Dow Limited, Tokyo, Japan

[21] Appl. No.: 793,342

[22] PCT Filed: Oct. 17, 1995

[86] PCT No.: PCT/JP95/02120

§ 371 Date: May 29, 1997

§ 102(e) Date: May 29, 1997

[87] PCT Pub. No.: WO96/11984

PCT Pub. Date: Apr. 25, 1996

[30] Foreign Application Priority Data

Oct. 18, 1994 [JP] Japan ................................. 6-279864
Aug. 28, 1995 [JP] Japan ................................. 7-243765

[51] Int. Cl.[6] ............................. G21F 1/10; C08K 5/49; C08K 5/06
[52] U.S. Cl. .................. 523/136; 524/119; 524/378; 524/390; 524/391; 524/384; 524/464; 524/500; 524/540; 524/611

[58] Field of Search ...................... 524/119, 378, 524/390, 391, 611, 464, 384, 500, 540; 523/136

[56] References Cited

FOREIGN PATENT DOCUMENTS 2-129261  5/1990  Japan .
2-163156  6/1990  Japan .
3-33115   2/1991  Japan .

*Primary Examiner*—Kriellion S. Morgan

[57] ABSTRACT

An ionizing radiation-resistant polycarbonate resin composition comprising 0.1 to 10 parts by weight of an organic compound having one carbon—carbon unsaturated double bond forming a non-bonding orbital in the molecule based on 100 parts by weight of a polycarbonate resin, and a medical part comprising the same. The polycarbonate resin composition and the medical part comprising the same exhibit less deterioration of color and physical properties even when irradiated with ionizing radiation for sterilization, and are, therefore, useful as a medical part material and a medical part.

8 Claims, No Drawings

IONIZING RADIATION-RESISTANT POLYCARBONATE RESIN COMPOSITION AND MEDICAL PART COMPRISING SAME

FIELD OF THE INVENTION

The present invention relates to an ionizing radiation-resistant polycarbonate resin composition and a medical part comprising the same. The present invention relates more in detail to a polycarbonate resin composition which exhibits no deterioration of color and physical properties even when it is irradiated with ionizing radiation for sterilization, and a medical part comprising such a composition.

CONVENTIONAL ART

A polycarbonate resin is excellent in mechanical and thermal properties, and used for wide applications. Moreover, since the polycarbonate resin has excellent transparency, sanitary properties, toughness and heat resistance, it is used, for example, for packaging parts having a container form for accommodating or packaging injectors, surgical tools, intravenous injectors, operation instruments, and the like, for parts of medical apparatuses such as artificial lungs, artificial kidneys, anesthetic inhalators, vein connectors and their accessaries and centrifugal separators for blood, and for medical parts for surgical tools and operation tools.

These medical parts are usually completely sterilized. Concretely, the sterilization is carried out by contacting them with ethylene oxide, heat treating them in an autoclave, or irradiating them with ionizing radiation such as γ-rays and an electron beam.

Among these sterilization procedures, the contact treatment with ethylene oxide is not preferred because ethylene oxide itself is toxic and unstable, and involves environmental problems related to waste treatment. Moreover, the heat treatment of the parts in an autoclave has disadvantages that the resin may be deteriorated during the treatment at high temperature, that its energy cost is high, and that the parts are required to be dried after the treatment due to remaining moisture.

Accordingly, in place of these procedures, sterilization by irradiation of the parts with ionizing radiation which can be carried out at low temperature at relatively low cost is employed.

However, the polycarbonate resin which is inherently optically transparent turns yellow when irradiated with ionizing radiation. Therefore, methods such as a method of mixing a blue colorant with the resin and a method of adding various additives for inhibiting the yellowing have been proposed.

For example, the following methods are known: a method of incorporating a polyester or a copolyester such as a polyester comprising 1,4-cyclohexyldimethanol and a six-membered carbocyclic dicarboxylic acid disclosed in EP-A-152825 and EP-A-226189; a method of incorporating a mercapto compound such as a thioglycol disclosed in Japanese Patent Kokai Publication Nos. 49058/1990, 115260/1990 and 36343/1992; a method of adding a polyether polyol such as polypropylene glycol, or its alkyl ether disclosed in U.S. Pat. No. 4,904,710, EP-A-296473, EP-A-338319, U.S. Pat. No. 4,874,802, EP-A-359366, U.S. Pat. Nos. 4,804,692 and 4,873,271 and EP-A-439763; a method of adding an epoxide compound disclosed in EP-A-272421; a method of adding a boron compound disclosed in EP-A-189583; a method of adding a polyfunctional monomer containing at least two aliphatic double bonds within the molecule disclosed in Japanese Patent Kokai Publication No. 33115/1991; and a method of adding a halogenated compound represented by a polycarbonate or copolycarbonate derived from a halogenated bisphenol A disclosed in Japanese Patent Kokai Publication Nos. 55062/1990 and 68068/1990 and EP-A-376289. Even these methods cannot sufficiently inhibit the yellowing of polycarbonate resins when the resins are irradiated with ionizing radiation.

Furthermore, various methods in which the additives as mentioned above or the compounds having functional groups as mentioned above are added in combination are proposed.

Examples of such methods are a method of adding a halogenated bisphenol A type epoxy compound disclosed in Japanese Patent Kokai Publication No. 7356/1992; a method of adding a halogenated bisphenol A and a thioether disclosed in Japanese Patent Kokai Publication No. 232259/1990; a method of adding a polyester containing a halogen atom disclosed in Japanese Patent Kokai Publication No. 11653/1992; a method of adding a compound having at least two aliphatic unsaturated double bonds and a halogenated compound in combination disclosed in Japanese Patent Kokai Publication No. 163156/1990; and a method of adding a halogenated compound, and a polyalkylene glycol or its derivative in combination disclosed in EP-A-359366, EP-A-376289, and Japanese Patent Kokai Publication Nos 7356/1992, 11653/1992 and 13759/1992.

However, the polycarbonate resins thus obtained by utilizing any of such methods have drawbacks that the resin exhibits no sufficient effects of preventing yellowing, and that the strength of the polycarbonate resin itself is markedly impaired when a sufficient amount of the additive is added so that the effects are manifested.

Neither materials which exhibit substantially less yellow discoloration at the time of sterilization by ionizing radiation and still maintain sufficient strength and toughness nor medical parts prepared therefrom are obtained.

SUMMARY OF THE INVENTION

An object of the present invention is to provide a polycarbonate resin which suffers from less color change and maintains its physical properties even when irradiated with ionizing radiation.

Another object of the present invention is to provide a medical part which can easily be disinfected and exhibits neither strength lowering nor discoloration when disinfected.

The present invention provides a polycarbonate resin composition and a medical part comprising a polycarbonate resin, an organic compound having only one carbon—carbon unsaturated double bond which forms a non-bonding orbital in a molecule as an aliphatic carbon—carbon double bond, and optionally at least one compound selected from the group consisting of a polyether polyol or its derivative, an organic halogenated compound and a phosphite compound.

This polycarbonate resin composition turns substantially less yellow when sterilized by ionizing radiation, and still maintains a sufficient strength and excellent stability to heat and light.

DETAILED DESCRIPTION OF THE INVENTION

The polycarbonate resin used in the present invention is a polymer obtained by a phosgene method wherein a dihydroxydiaryl compound of various type is reacted with phosgene or a transesterification method wherein a dihydroxydiaryl compound is reacted with a carbonate ester such as diphenyl carbonate, and a typical example thereof is a polycarbonate resin prepared from 2,2-bis(4-hydroxyphenyl)propane (bisphenol A).

Examples of the dihydroxydiaryl compound other than bisphenol A are bis(hydroxyaryl)alkanes such as bis(4-hydroxyphenyl)methane, 1,1-bis(4-hydroxyphenyl)ethane, 2,2-bis(4-hydroxyphenyl)butane, 2,2-bis(4-hydroxyphenyl) octane, bis(4-hydroxyphenyl)phenylmethane, 2,2-bis(4-hydroxyphenyl-3-methylphenyl)propane, 1,1-bis(4-hydroxy-3-tert-butylphenyl)propane, 2,2-bis(4-hydroxy-3-bromophenyl)propane, 2,2-bis(4-hydroxy-3,5-dibromophenyl)propane and 2,2-bis(4-hydroxy-3,5-dichlorophenyl)propane; bis(hydroxyaryl)cycloalkanes such as 1,1-bis(4-hydroxyphenyl)cyclopentane and 1,1-bis(4-hydroxyphenyl)cyclohexane; dihyroxydiaryl ethers such as 4,4'-dihydroxydiphenyl ether and 4,4'-dihydroxy-3,3'-dimethyldiphenyl ether; dihydroxydiaryl sulfides such as 4,4'-dihydroxydiphenyl sulfide and 4,4'-dihydroxy-3,3'-dimethyldiphenyl sulfide; dihydroxydiaryl sulfoxides such as 4,4'-dihydroxydiphenyl sulfoxide and 4,4'-dihydroxy-3, 3'-dimethyidiphenyl sulfoxide; dihydroxydiaryl-sulfones such as 4,4'-dihydroxydiphenylsulfone and 4,4'-dihydroxy-3,3'-dimethyidiphenylsulfone, and the like. These compounds may be used independently or as a mixture of at least two of them. These compounds may also be used as a mixture with a compound such as piperazine, dipiperidylhydroquinone, resorcinol and 4,4'-dihydroxydiphenyl.

Furthermore, the above dihydroxyaryl compound and a phenol compound which is at least trihydric as shown below may be mixed and used.

Examples of the phenol which is at least trihydric are phloroglucine, 4,6-dimethyl-2,4,6-tri-(4-hydroxyphenyl)-heptene-2, 4,6-dimethyl-2,4,6-tri(4-hydroxyphenyl)heptane, 1,3,5-tri-(4-hydroxyphenyl)benzole, 1,1,1-tri-(4-hydroxyphenyl)ethane, 2,2-bis[4,4-(4,4'-dihydroxydiphenyl)cyclohexyl]propane, and the like. These compounds may be used independently or as a mixture of at least two of them.

Although there is no specific limitation on the viscosity-average molecular weight of the polycarbonate resin, the molecular weight is usually from 10,000 to 100,000, preferably from 15,000 to 35,000 in view of the moldability and the strength. Moreover, in the preparation of such the polycarbonate resin, optionally a molecular weight modifier, a catalyst, and the like may be used.

The organic compound which has one carbon—carbon unsaturated double bond forming a non-bonding orbital in the molecule as an aliphatic carbon—carbon double bond and as used in the present invention has a known conception in the molecular orbital theory. For example, as disclosed in Morrison and Boyd, *Organic Chemistry, II*, fifth edition, published on Jun. 6, 1989 by Tokyo Kagaku Dojin, when an allyl cation, an allyl anion or an allyl radical is formed in the case of an allyl group which has a carbon atom adjacent to a carbon—carbon double bond, a non-bonding orbital is formed, and a bonding orbital is stabilized, whereby the product formed is stabilized.

Examples of the organic compound used in the present invention which has one carbon—carbon unsaturated double bond forming a non-bonding orbital in the molecule are allyl alcohol and its derivatives, an allyl ether compound and its derivatives, α-methylstyrene dimer and its derivatives, and the like. Examples of allyl alcohol and its derivatives are allyl alcohol, allylacetic acid, and esters such as allyl hexanoate, allyl butanoate and allyl decanoate.

Examples of the allyl ether compound and its derivatives are p-allylanisole, apiol, allyltrimethylsilane, elemicine (5-allyl-1,2,3-trimethoxybenzene), 5-allyl-5-neopentylbarbituric acid, 5-allyl-5-(2-hydroxypropyl) barbiuric acid, 5-allyl-5-(1-methylbutyl)barbituric acid, chavibetol (4-allyl-2-hydroxy-1-methoxybenzene), 4-allyl-methoxyphenol, allyl phenyl ether, allylphenol, allylbenzene, allylmalonic acid, monoallyl ethers such as monoallyl glycerol ether and monoallyl pentaerythritol, a polyalkylene glycol monoallyl ether and its monoalkyl ethers such as polyethylene glycol monoallyl ether, polypropylene glycol monoallyl ether and polyethylene polypropylene glycol monoallyl ether, and the like. In addition, although there is no specific limitation on the molecular weight of the polyalkylene glycol monoallyl ether and its monoalkyl ethers, the molecular weight is preferably from 200 to 3,000.

Examples of α-methylstyrene dimer and its derivatives are α-methylstyrene dimer, α-methylstyrene trimer, and the like.

The organic compound having one carbon—carbon unsaturated double bond forming a non-bonding orbital in the molecule in the present invention is incorporated in an amount of 0.1 to 10 parts by weight, preferably 0.3 to 5 parts by weight based on 100 parts by weight of the polycarbonate resin. When the amount is less than 0.1 part by weight, an ionization radiation resistance of the resin composition cannot be sufficiently improved. When the amount exceeds 10 parts by weight, the resin is deteriorated during molding, and the physical properties of the final products are lowered.

Examples of the polyether polyol and its derivative in the present invention are compounds represented by the general formulas (2) to (8) mentioned below. One or more of these compounds may be used. Among such compounds, the compounds represented by the general formula (2) are preferred, and polypropylene glycol is particularly preferred.

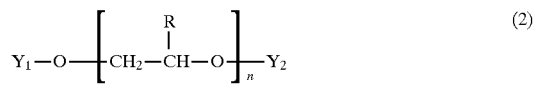

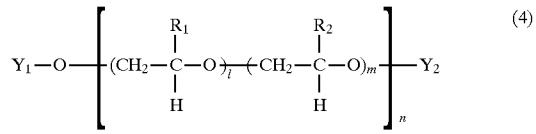

In the general formulas (2) to (4), R, $R_1$ and $R_2$ are each independently a hydrogen atom, a halogen atom, an alkyl group of 1 to 10 carbon atoms, an aryl group of 6 to 10 carbon atoms, an alkylaryl group of 6 to 18 carbon atoms or a cycloalkyl group of 4 to 10 carbon atoms, n is an integer of at least 1, preferably 1 to 1,000, m is an integer of at least 1, preferably 1 to 1,000, l is an integer of at least 1, preferably 1 to 1,000, and $Y_1$ and $Y_2$ are each independently a hydrogen atom, an alkyl group of 1 to 10 carbon atoms, an aryl group of 6 to 10 carbon atoms, an alkylaryl group of 6 to 18 carbon atoms, a cycloalkyl group of 4 to 10 carbon atoms or $Y_3$—CO— (wherein $Y_3$ is an alkyl group of 1 to 20 carbon atoms, an aryl group of 6 to 10 carbon atoms, an alkylaryl group of 6 to 18 carbon atoms or a cycloalkyl group of 4 to 10 carbon atoms).

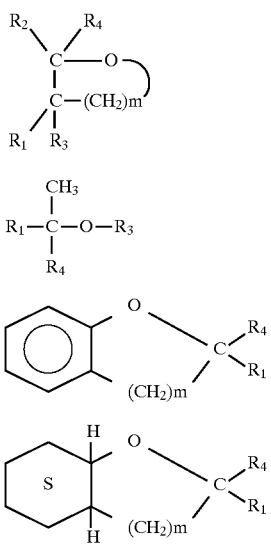

(5)

(6)

(7)

(8)

In the general formulas (5) to (8), m is 1 or 3 to 6, $R_1$ to $R_4$ are each independently a hydrogen atom, an alkyl group of 1 to 10 carbon atoms, an aryl group of 6 to 10 carbon atoms or an alkylaryl group of 6 to 18 carbon atoms.

The polyether polyol or its derivative is used in an amount of 0.1 to 5 parts by weight based on 100 parts by weight of the polycarbonate resin. When 0.1 to 10 parts by weight of the organic compound having one carbon—carbon double bond forming a non-bonding orbital in the molecule and 0.1 to 5 parts by weight of the polyether polyol or its derivative are used in combination, excellent synergistic effects on ionizing radiation resistance can be obtained.

The organic halogenated compound in the present invention is a compound containing a halogen atom in the molecule. Examples of the compound are halogenated benzenes such as hexabromobenzene and pentabromotoluene; halogenated diphenyls such as tetrabromodiphenyl, decabromodiphenyl, tetrabromodiphenyl ether, decabromodiphenyl ether and decabromodiphenylsulfone; halogenated bisphenol A or its derivatives such as 2,2-bis(4-hydroxy-3,5-dibromo-phenyl)propane [tetrabromobisphenol A], 2,2-bis(4-glycidoxy-3,5-dibromophenyl)propane or the low polymerization product [halogenated bisphenol A epoxy resin], 2,2-bis(4-hydroxyethoxy-3,5-dibromophenyl) propane, 2,2-bis(4-acethoxy-3,5-dibromophenyl)propane and a polycarbonate oligomer of tetrabromobisphenol A; a copolycarbonate of bisphenol A and tetrabromobisphenol A, tetrabromophthalic anhydride, a condensation product of tribromophenol, polypentabromobenzyl acrylate, bromostyrene, a condensation product of tetrabromobisphenol A, cyanuric acid and tribromophenol, and the like. These compounds may be used independently or as a mixture of at least two of them.

Among these compounds, the copolycarbonate of bisphenol A and tetrabromobisphenol A is particularly preferred.

The organic halogenated compound is contained in an amount of 0.1 to 10 parts by weight in terms of halogen atoms based on 100 parts by weight of the polycarbonate resin. When 0.1 to 10 parts by weight of the organic compound having one carbon—carbon double bond forming a non-bonding orbital in the molecule and 0.1 to 10 parts by weight in terms of halogenated atoms of the organic halogenated compound are used in combination, excellent synergistic effects on ionizing radiation resistance can be obtained.

The present invention can provide an ionizing radiation-resistant polycarbonate resin composition having not only ionizing radiation resistance but also excellent properties against heat and light, namely excellent stability by incorporating a phosphite compound represented by the general formula (1) described below into the composition as mentioned above.

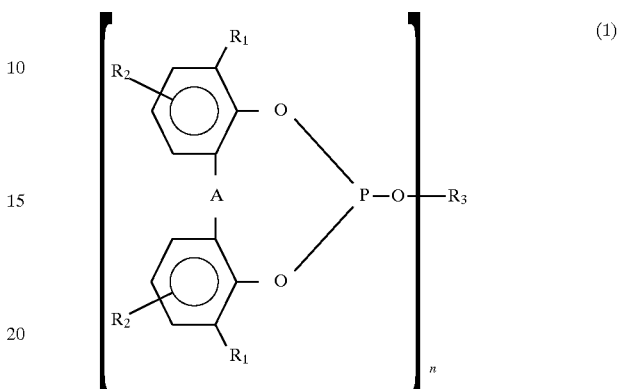

(1)

wherein A is a sulfur atom, an oxygen atom or an alkylidene group such as a methylene group, an ethylidene group, an isopropylidene group and a butylidene group, $R_1$ is an alkyl group such as a methyl group, an ethyl group, an isopropyl group, an octyl group, a lauryl group and a benzyl group, $R_2$ is a hydrogen atom or an alkyl group such as a methyl group, an ethyl group, an isopropyl group, an octyl group, a lauryl group and a benzyl group, $R_3$ is from 2 to 4 alcohol residues such as a residue of ethylene glycol, diethylene glycol, 1,2-propanediol, neopentyl glycol or 1,6-hexanediol, or three polynuclear phenol residues such as a residue of tris(3,5-di-tert-butyl-4-hydroxybenzyl)isocyanurate or 1,1,3-tris(2-methyl-4-hydroxy-5-tert-butylphenyl)butane, and n is from 2 to 4.

2,2-Methylenebis(4,6-di-tert-butylphenyl)octyl phosphite is particularly preferred.

Although there is no specific limitation on the addition amount of the phosphite compound represented by the general formula (1), the addition amount is preferably from 0.001 to 10 parts by weight, particularly from 0.01 to 1 part by weight based on 100 parts by weight of the polycarbonate resin. When the addition amount is less than 0.001 part by weight, sufficient effects of improving the stability cannot be obtained by the addition thereof. When the addition amount exceeds 10 parts by weight, the physical properties inherent to the polycarbonate resin are impaired.

As a manner for incorporating, into the polycarbonate resin, the organic compound having one carbon—carbon unsaturated double bond forming a non-bonding orbital in the molecule, the organic compound and the polyether polyol or its derivative, the organic compound and the organic halogenated compound, or the organic compound, any of the above-mentioned compounds other than the organic compound and the phosphite compound, any of methods known to those skilled in the art may be employed at any freely selected step until just before molding to obtain the final molded article. For example, the organic compound having one carbon—carbon unsaturated double bond forming a non-bonding orbital in the molecule and the above-mentioned compounds (the polyether polyol or its derivative, the organic halogenated compound and the phosphite compound) may be compounded in the resin prior to, during or after polymerization of the polycarbonate resin, or the polycarbonate resin obtained by polymerization may be mixed with the organic compound having one carbon—carbon unsaturated double bond forming a non-bonding orbital in the molecule, or with the organic compound and the above-mentioned compounds (the polyether polyol or its derivative, the organic halogenated compound and the phosphite compound) with a tumbling mixer, a ribbon blender, a high speed mixer and the like. The resulting mixture is then molten and kneaded by a single or twin screw extruder. There is no limitation in the order of compounding the above-mentioned compounds (the polyether polyol or its derivative, the organic halogenated compound and the phosphite compound) used in combination with the organic compound having one carbon—carbon unsaturated double bond forming a non-bonding orbital in the molecule. These compounds may be incorporated simultaneously, or they may be incorporated in an arbitrary order.

Other resin may be added to the ionizing radiation-resistant polycarbonate resin composition of the present invention so long as the effects of the present invention are not impaired. For example, a small amount of polyethylene terephthalate, polybutylene terephthalate, polyester polycarbonate, a polycondensation product of cyclohexanedimethanol with terephthalic acid and/or isophthalic acid or a copolymer of the polycondensation product with a polyethylene terephthalate, or the like may be added to the resin composition.

Furthermore, other known ionizing radiation resistance improvers such as a polyester, a mercapto compound, an epoxide compound, a boron compound, a polyfunctional monomer and a halogenated compound, various additives such as a hydrolysis inhibitor (e.g., an epoxy compound), a lubricant (e.g., paraffin wax and an aliphatic acid ester), an antioxidant (e.g., a hindered phenol, a phosphoric acid ester and a phosphorous acid ester), a weathering improver (e.g., a triazine compound), a flame retardant (e.g., a halogen type or phosphoric acid type one) and a colorant (e.g., a pigment and a dye), and the like.

The ionizing radiation-resistant polycarbonate resin composition of the present invention is processed to give a medical part by a method known to those skilled in the art. Examples of the medical part are packaging parts having a container form for accommodating or packaging injectors, surgical tools, intravenous injectors, operation instruments, and the like, for parts of medical apparatuses such as artificial lungs, artificial kidneys, anesthetic inhalators, vein connectors and their accessaries and for parts of centrifugal separators for blood, surgical tools, operation tools, and the like. There is no specific limitation on the processing method. For example, any of molding methods such as injection molding, extrusion molding, blow molding and press molding may be applied, and the resin composition may be molded under conditions similar to those of molding a known polycarbonate resin and a known ionizing radiation-resistant improved polycarbonate resin.

Examples of the ionizing radiation are α-rays, a heavy electron beam, a proton beam, β-rays, an electron beam, a neutron beam, γ-rays and X-rays. However, γ-rays are industrially used. Although there is no specific limitation on the amount of ionizing radiation to be irradiated, the amount is usually from 20 to 30 kgray.

EXAMPLES

The present invention will be illustrated by the following examples, which will not limit the scope of the present invention.

Examples 1 to 4 and Comparative Examples 1 to 3

Additives shown in Table 1 were added to 100 parts by weight of pellets of a polycarbonate resin (viscosity average molecular weight of 21,000). The mixture was thoroughly blended by a tumbling mixer, and pelletized in a conventional way by a 40-mm single screw extruder. The pellets thus obtained were molded by injection molding at 300° C. without residence in a molding cycle of 40 seconds to obtain a test plate having a size of 45 mm×55 mm×3 mm. Table 1 shows a YI value of the original plate obtained at the second shot and a YI value of the plate after treating the plate with γ-rays at 25 kgray.

Additive A: α-methylstyrene dimer

Additive B: polypropylene glycol having a molecular weight of 2,000

Additive C: oligomer of tetrabromobisphenol A with terminal phenoxy groups, having a molecular weight of 2,500.

TABLE 1

| | Types and amounts of additives (parts by weight) | | | YI value before irradiation of | YI value after irradiation of |
|---|---|---|---|---|---|
| | A | B | C | γ-rays | γ-rays |
| Comp. Ex. 1 | 0 | 0 | 0 | 1.6 | 28.0 |
| Comp. Ex. 2 | 0 | 0.9 | 0 | 1.6 | 18.6 |
| Comp. Ex. 3 | 0 | 0.9 | 5.0 | 1.7 | 13.3 |
| Ex. 1 | 1.0 | 0 | 0 | 1.5 | 9.9 |
| Ex. 2 | 1.0 | 0.9 | 0 | 1.5 | 8.7 |
| Ex. 3 | 3.0 | 0 | 0 | 1.5 | 7.3 |
| Ex. 4 | 3.0 | 0.9 | 5.0 | 1.5 | 5.5 |

Examples 5 to 9 and Comparative Example 4

Additives as shown below were added to 100 parts by weight of pellets of a polycarbonate resin (viscosity average molecular weight of 24,000). The mixture was thoroughly blended by a tumbling mixer, and pelletized in the conventional way by a 40-mm single screw extruder. The mixing formulations are shown in Table 2. The pellets thus obtained were molded by injection molding at 300° C. without residence in a molding cycle of 40 seconds to obtain a test plate having a size of 45 mm×55 mm×3 mm. Table 2 shows a YI value of the original plate obtained at the second shot and a YI value of the plate after treating the plate with γ-rays of 32 kgray.

Additive D: polyethylene glycol monoallyl ether of the following formula:

$$CH_2=CHCH_2O(EO)_nH$$

having an average molecular weight of 200.

Additive E: polyethylene glycol monoallyl ether of the formula:

$$CH_2=CHCH_2O(EO)_nH$$

having an average molecular weight of 1,500.

Additive F: polyethylene glycol methyl allyl ether of the formula:

$$CH_2=CHCH_2O(EO)_nCH_3$$

having an average molecular weight of 1,500.

Additive G: polyethylene polypropylene glycol monoallyl ether of the formula:

$$CH_2=CHCH_2O[(EO)_m(PO)_n]H$$

(m:n=1:1)

in which the ratio of ethylene oxide units to propylene oxide units is 50/50, and which has an average molecular weight of 2,000.

Additive H: polyethylene polypropylene glycol butyl allyl ether of the formula:

$$CH_2=CHCH_2O[(EO)_m(PO)_n]C_4H_9$$

(m:n=1:1)

in which the ratio of ethylene oxide units to propylene oxide units is 50/50, and which has an average molecular weight of 1,600.

TABLE 2

| | Type and amount of additive (part by weight) | | | | | YI value before or after irradiation | |
|---|---|---|---|---|---|---|---|
| | D | E | F | G | H | Before | After |
| Comp. Ex. 4 | — | — | — | — | — | 1.8 | 20.0 |
| Ex. 5 | 0.9 | — | — | — | — | 1.3 | 5.0 |
| Ex. 6 | — | 0.9 | — | — | — | 1.4 | 7.6 |
| Ex. 7 | — | — | 0.9 | — | — | 1.2 | 8.0 |
| Ex. 8 | — | — | — | 0.9 | — | 1.2 | 8.3 |
| Ex. 9 | — | — | — | — | 0.9 | 1.3 | 7.7 |

Examples 10 to 11

Additive F used in Example 6 and Additive B and/or Additive C used in Comparative Example 3 were added according to the formulations shown in Table 3 to 100 parts by weight of pellets of a polycarbonate resin (viscosity average molecular weight of 24,000). The mixture was thoroughly blended by a tumbling mixer, and pelletized in the conventional way by a 40-mm single screw extruder. The pellets thus obtained were molded by injection molding at 300° C. without residence in a molding cycle of 40 seconds to obtain a test plate having a size of 45 mm×55 mm×3 mm. Table 3 shows a YI value of the original plate obtained at the second shot and a YI value of the plate after treating the plate with γ-rays at 32 kgray.

TABLE 3

| | Types and amounts of additives (parts by weight) | | | YI value before irradiation of | YI value after irradiation of |
|---|---|---|---|---|---|
| | E | B | C | γ-rays | γ-rays |
| Comp. Ex. 4 | 0 | 0 | 0 | 1.8 | 20.0 |
| Comp. Ex. 5 | 0 | 0.9 | 0 | 1.3 | 14.1 |
| Comp. Ex. 6 | 0 | 0.9 | 5.0 | 1.4 | 11.9 |
| Ex. 6 | 0.9 | 0 | 0 | 1.4 | 7.6 |
| Ex. 10 | 0.9 | 0.9 | 0 | 1.5 | 6.9 |
| Ex. 11 | 0.9 | 0.9 | 5.0 | 1.7 | 5.1 |

Examples 12 to 14

Additives B and C used in Comparative Example 3 and Additive I mentioned below were added according to the formulations as shown in Table 4 to 100 parts by weight of pellets of a polycarbonate resin (viscosity average molecular weight of 24,000). The mixture was thoroughly blended by a tumbling mixer, and pelletized in the conventional way by a 40-mm single screw extruder. The pellets thus obtained were molded by injection molding at 300° C. without residence at a molding cycle of 40 seconds to obtain a test plate having a size of 45 mm×55 mm×3 mm. Table 4 shows a YI value of the original plate obtained at the second shot and a YI value of the plate after treating the plate with γ-rays at 32 kgray.

Additive I: allyl decanoate

TABLE 4

| | Types and amounts of additives (parts by weight) | | | YI value before irradiation of | YI value after irradiation of |
|---|---|---|---|---|---|
| | I | B | C | γ-rays | γ-rays |
| Comp. Ex. 4 | 0 | 0 | 0 | 1.8 | 20.0 |
| Comp. Ex. 5 | 0 | 0.9 | 0 | 1.3 | 14.1 |
| Comp. Ex. 6 | 0 | 0.9 | 5.0 | 1.4 | 11.9 |
| Ex. 12 | 0.9 | 0 | 0 | 1.4 | 9.2 |
| Ex. 13 | 0.9 | 0.9 | 0 | 1.5 | 8.3 |
| Ex. 14 | 0.9 | 0.9 | 5.0 | 1.7 | 6.5 |

Examples 15 to 17 and Comparative Example 7

Additives as shown in Table 5 were added to 100 parts by weight of pellets of a polycarbonate resin (viscosity average molecular weight of 21,000). The mixture was thoroughly blended by a tumbling mixer, and pelletized in the conventional way by a 40-mm single screw extruder. The pellets thus obtained were molded by injection molding at 340° C. while the molten resin was retained within the cylinder of the molding machine for 15 minutes to obtain a test plate having a size of 45 mm×55 mm×3 mm. Table 5 shows a YI value of the original plate obtained at the second shot and a YI value of the plate after treating the plate with γ-rays at 25 kgray.

Additive A: α-methylstyrene dimer.

Additive C: oligomer of tetrabromobisphenol A with terminal phenoxy groups, having a molecular weight of 2,500.

Additive D: polyethylene glycol monoallyl ether of the formula:

$$CH_2=CHCH_2O(EO)_nH$$

having an average molecular weight of 200.

Additive J: 2,2-methylenebis(4,6-di-tert-butylphenyl) octyl phosphite.

TABLE 5

| | Types and amounts of additives (parts by weight) | | | | Retained molded article | |
|---|---|---|---|---|---|---|
| | | | | | YI value before irradiation of | YI value after irradiation of |
| | A | C | D | J | γ-rays | γ-rays |
| Comp. Ex. 7 | 0 | 0 | 0 | 0.2 | 1.6 | 27.8 |
| Ex. 15 | 1.0 | 0 | 0 | 0.1 | 1.8 | 8.5 |
| Ex. 16 | 3.0 | 3.5 | 0 | 0.2 | 1.5 | 7.6 |
| Ex. 17 | 0 | 0 | 0.5 | 0.3 | 1.5 | 5.3 |

EFFECTS

The ionizing radiation-resistant polycarbonate resin composition and the medical parts comprising the same of the present invention extremely less turn yellow and still maintain strength and toughness when sterilized with ionizing radiation, and are useful as materials for medical parts to be sterilized with ionizing radiation.

What is claimed is:

1. An ionizing radiation-resistant polycarbonate resin composition comprising 100 parts by weight of a polycarbonate resin and 0.1 to 10 parts by weight of an organic compound having only one carbon—carbon unsaturated double bond forming a non-bonding orbital in a molecule as an aliphatic carbon—carbon double bond.

2. The ionizing radiation-resistant polycarbonate resin composition according to claim 1, which comprises 0.3 to 5 parts by weight of allyl alcohol and/or its derivative as the organic compound having only one carbon—carbon unsaturated double bond forming a non-bonding orbital in the molecule as an aliphatic carbon—carbon double bond.

3. The ionizing radiation-resistant polycarbonate resin composition according to claim 1, which comprises 0.3 to 5 parts by weight of an allyl ether compound and/or its derivative as the organic compound having only one carbon—carbon unsaturated double bond forming a non-bonding orbital in the molecule as an aliphatic carbon—carbon double bond.

4. The ionizing radiation-resistant polycarbonate resin composition according to claim 1, which comprises from 0.3 to 5 parts by weight of α-methylstyrene dimer and/or its derivative as the organic compound having only one carbon—carbon unsaturated double bond forming a non-bonding orbital in the molecule as an aliphatic carbon—carbon double bond.

5. The ionizing radiation-resistant polycarbonate resin composition according to any one of claims 1 to 4, which comprises 0.1 to 5 parts by weight of a polyether polyol and/or its derivative.

6. The ionizing radiation-resistant polycarbonate resin composition according to any one of claims 1 to 4, which comprises 0.1 to 10 parts by weight of an organic halogenated compound on a halogen atoms basis.

7. The ionizing radiation-resistant polycarbonate resin composition according to any one of claims 1 to 4, which comprises 0.001 to 10 parts by weight of a phosphite compound represented by the general formula (1)

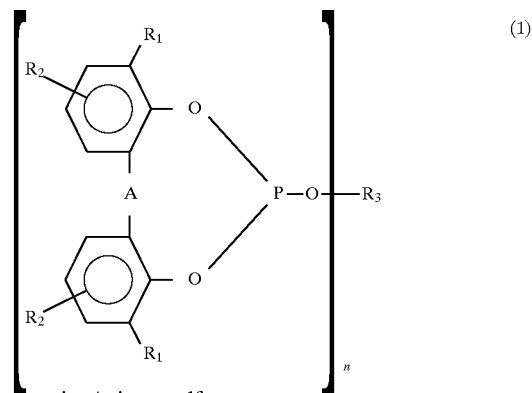

wherein A is a sulfur atom, an oxygen atom or an alkylidene group, $R_1$ is an alkyl group, $R_2$ is a hydrogen atom or an alkyl group, $R_3$ is from 2 to 4 alcohol residues or 3 polynuclear phenol residues, and n is 2 to 4.

8. A medical part comprising the ionizing radiation-resistant polycarbonate resin composition according to any one of claims 1 to 4.

* * * * *